(12) United States Patent
Sun et al.

(10) Patent No.: US 6,273,856 B1
(45) Date of Patent: Aug. 14, 2001

(54) APPARATUS AND METHODS FOR METS MEASUREMENT BY ACCELEROMETER AND MINUTE VENTILATION SENSORS

(75) Inventors: Weimin Sun, Plymouth; Bruce R. Jones, Hopkins; Donald L. Hopper, Maple Grove; Wyatt K. Stahl, Vadnais Heights, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/421,017

(22) Filed: Oct. 19, 1999

(51) Int. Cl.[7] ........................................ A61B 5/00
(52) U.S. Cl. ...................... 600/300; 607/19; 607/20; 482/8
(58) Field of Search ..................... 600/300, 509, 600/520, 595; 607/17, 29, 20; 482/8, 9

(56) References Cited

U.S. PATENT DOCUMENTS

| | | | |
|---|---|---|---|
| 4,702,253 | 10/1987 | Nappholz et al. | 128/419 PG |
| 4,919,136 | 4/1990 | Alt | 128/419 P |
| 4,926,863 | 5/1990 | Alt | 128/419 PG |
| 5,318,597 | 6/1994 | Hauck et al. | 607/20 |
| 5,376,106 | 12/1994 | Stahmann et al. | 607/18 |
| 5,976,083 | * 11/1999 | Richardson et al. | 600/300 |

* cited by examiner

Primary Examiner—William E. Kamm
(74) Attorney, Agent, or Firm—Nikolai, Mersereau & Dietz, P.A.

(57) ABSTRACT

Exertion levels of a patient are measured by monitoring signals from adaptive-rate sensors such as an accelerometer and or a minute ventilation sensor; sensor data is collected for conversion into metabolic equivalent measurements. The data obtained can be used to evaluate patient physical activity levels and can be used to assess the patient's condition and change pacing therapy or other treatments accordingly. An automatic adjustment of the adaptive-rate pacing therapy may be based on the activity levels detected by the metabolic equivalent measurements made by the pacemaker.

41 Claims, 1 Drawing Sheet

APPARATUS AND METHODS FOR METS MEASUREMENT BY ACCELEROMETER AND MINUTE VENTILATION SENSORS

BACKGROUND OF THE INVENTION

I. Field of the Invention

This invention relates to monitoring a patient's metabolic need over time, and more particularly to measuring metabolic equivalent (NETS) levels from sensors used in adaptive rate cardiac stimulators including, but not limited to, minute ventilation sensors and accelerometers, whereby patient metabolic equivalent rates and exercise events can be tracked and monitored.

II. Description of the Related Art

In order to measure metabolic equivalents it has been necessary in the past to measure the oxygen uptake (VO2) of a patient. This is difficult to do, particularly outside of a laboratory setting, in that it is necessary to have the patient equipped with respiratory monitoring devices, such as a breathing mask and sample tube, a gas analyzer, ekg leads, an electronics module for processing the parameters being monitored, etc.

Some models of calculating metabolic equivalents are based on the patient's intrinsic heart rate, but chronotropically incompetent pacemaker patients, of course, need a different model.

A method is therefore needed to monitor a patient in order to provide a physician with METS data and exertion levels, during the patient's normal living activity, without performing difficult exercise-based, oxygen uptake measurements. The measurements taken are needed to assess the lifestyle, exertion level, exercise capacity, cardiovascular functional capacity, quality of life and wellness of a patient for overall therapy management.

A method is also needed for changing the pacing parameters of a pacemaker based on current METS.

SUMMARY OF THE INVENTION

The invention provides metabolic equivalents data (METS) derived from an accelerometer (XL) and/or minute ventilation sensor (MV) used in rate-responsive pacemakers implanted in patients. Pacemakers commonly used today already have these sensors for providing rate adaption so patients need not be subjected to wearing a breathing mask or other devices to obtain the exertion level data needed to assess their well being.

The data collected is presented to a physician to show rates of excursion and exertion levels experienced by a patient using the pacemaker. The physician can then vary the therapy being provided by, for example, adjusting the pacemaker's rate, AV delay or other programmable quantity accordingly.

The accelerometer and minute ventilation sensor data obtained by the pacemaker can be stored in memory and a microprocessor can be programmed to manipulate the data into forms useful for the physician. Such useful forms include daily maximum exertion levels, average daily exertion levels, moving average exertion levels, exertion levels above a certain threshold, the number of times per day that the exertion levels are above the threshold and the duration of time above a threshold. The diagnostic reports to the physician can be transmitted to the physician and presented as daily, weekly, monthly or yearly data in graphic or tabular form.

The method employed for assessing patient well-being in accordance with the present invention is carried out by implanting in the patient a cardiac rhythm management device having a cardiac depolarization sensor, a physiologic sensor that produces electrical signals proportional to patient activity, a pulse generator for applying stimulating pulses to the heart and a microprocessor-based controller that is coupled to receive the output from the cardiac depolarization sensor along with the electrical signals from the physiologic sensor for producing delta rate signals for the pulse generator. The microprocessor-based controller is equipped with a memory whereby the delta rate signals may be stored for later readout. The microprocessor in the microprocessor based controller, is programmed to compute an average of the stored delta rate signals over a first pre-determined time interval. This average is used as an operand in a linear regression formula whereby a metabolic equivalent (METS) may be computed.

In accordance with a further feature of the invention, the physiologic sensor may be one or both of an accelerometer for sensing body motion and a transthoracic impedance sensor from which a minute ventilation signal can be derived. On a daily or weekly basis the maximum METS value and the average MET value for the interval in question can be computed and stored.

OBJECTS OF THE INVENTION

It is a principal object of the invention to provide a physician with metabolic need, physical activity and lifestyle information about a patient to evaluate the pacing parameters for the patient.

It is another object of the invention to measure and record maximal and average METS for various time periods.

It is yet another object of the invention to provide a method and apparatus for recording maximal MET, average MET, exercise frequency, and duration for storage whereby trended daily or weekly variations can be followed.

It is a further object of the invention to provide ambulatory activity monitoring and assessment in pacemaker patients, especially those suffering from CHF.

It is an object of the invention to improve management of pacing therapy.

It is an object of the invention to optimize rate responsive pacing.

It is still another object of the invention to change pacing therapy based on the MET measurements automatically.

It is an object of the invention to determine a patient's exertion level and exercise capacity.

It is also an object of the invention to monitor a patient to improve his quality of life and wellness.

DESCRIPTION OF THE DRAWINGS

Other objects, advantages and novel features of the present invention will become apparent from the following detailed description of the invention when considered in conjunction with the accompanying drawing in which.

DESCRIPTION OF THE PREFERRED EMBODIMENTS

Figure 1:
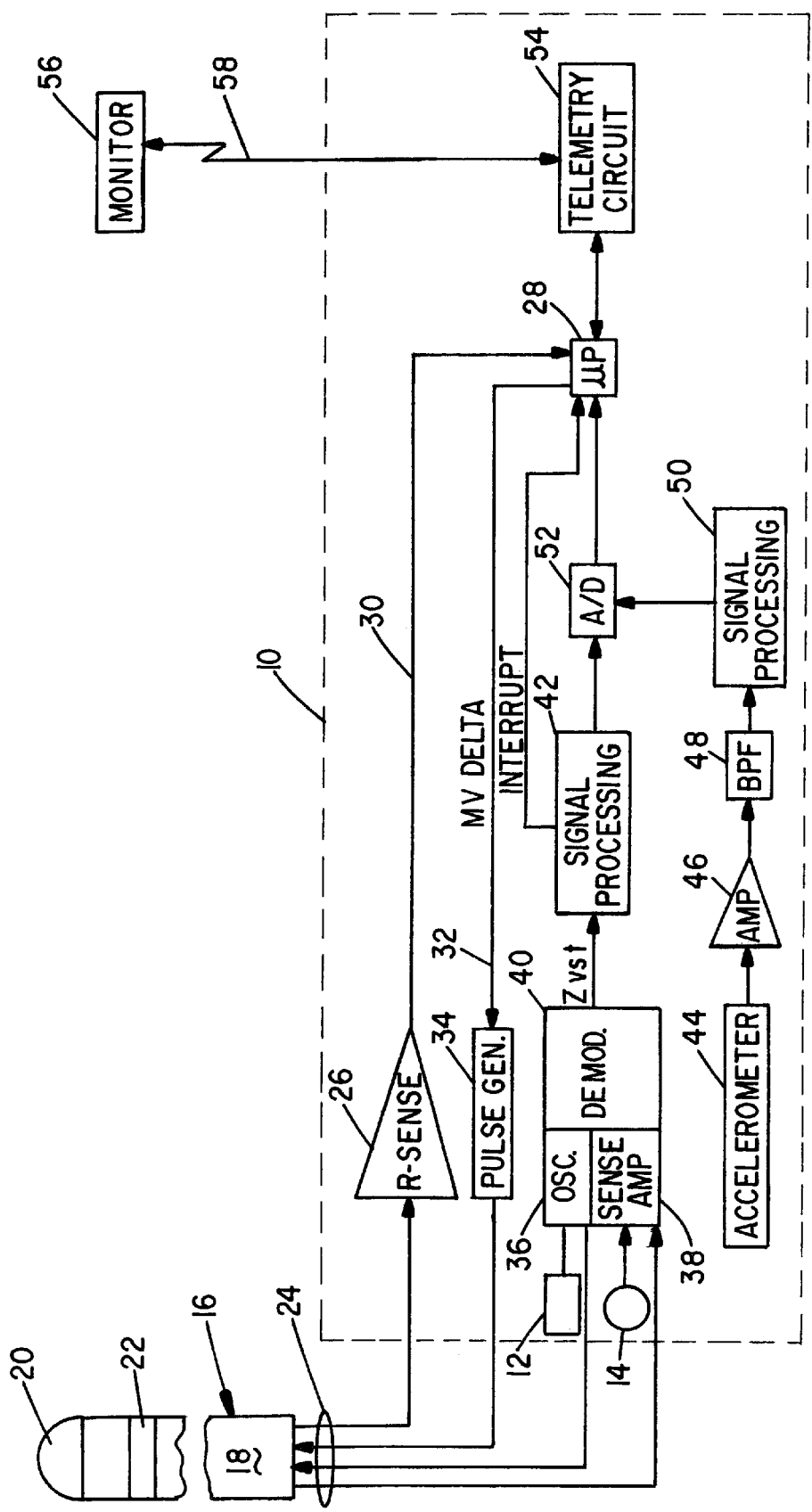
FIG. 1 is a block diagram of an implantable cardiac rhythm management device in which the present invention may be implemented.

Referring to FIG. 1 there is illustrated by means of an electrical schematic block diagram the hardware platform whereby the method of the present invention can be carried out. Shown enclosed by a broken line box 10 is an implantable CRM device having dual indifferent electrodes 12 and 14 disposed thereon. The electrode 12 may comprise an uninsulated portion of the metal (titanium) hermetically sealed housing while electrode 14 may be disposed on the device's header. The CRM device 10 is adapted to be coupled to a patient's heart via an electrical lead assembly 16 comprising an elongated flexible plastic tubular body member 18 having a distal tip electrode 20 and a ring electrode 22 affixed to the surface thereof. Extending the length of the lead are electrical conductors 24 that connect through electrical contacts in the lead barrel to the internal circuitry of the CRM device.

Contained within the hermetically sealed housing is a R-wave sensing amplifier 26 which picks up and amplifies ventricular depolarization signals picked up by the electrode 20. The output from the sense amplifier is applied as an input to a microprocessor circuit 28 by way of conductor 30. The microprocessor, following a stored program, provides a control signal on line 32 to a pulse generator 34 whose output signal is applied over one of the conductors 24 to the tip electrode 20 for stimulating and thereby evoking a paced response from the heart.

In accordance with the present invention, circuitry is also provided for measuring impedance changes within at least one chamber of the heart due to the influx and outflow of blood. In this regard, there is provided an oscillator 36 which, when activated, produces an alternating current of a predetermined frequency, typically in a range of from about 2000 Hz to 5000 Hz and of an amplitude below about 10 microamperes, which insures that the output from the oscillator will not stimulate heart tissue. This signal is preferably applied between the indifferent electrode 12 on the implanted CRM device and the tip electrode 20 on the lead and comprises an AC carrier signal that is modulated by the influx and outflow blood from the right ventricle. The modulated carrier signal is developed between the ring electrode 22 and the indifferent electrode 14 on the device's header and is amplified by sense amplifier 38 and then demodulated by demodulator circuit 40 to remove the modulating envelope from the carrier. The envelope signal is a measure of instantaneous impedance as a function of time.

The impedance vs. time (Z vs. t) is then applied to a signal processing circuit 42 which comprises a peak/valley/zero cross detector. When a zero cross is detected, the circuit 42 calculates the preceding peak-to-valley amplitude and issues an interrupt signal to the microprocessor 28. Upon receiving this interrupt, the microprocessor fetches the peak-to-valley amplitude from the signal processing circuit 42 and sums the absolute values of the peak-to-valley amplitudes over an eight-second interval. This eight-second sum of the peak-to-valley amplitudes comprises the sensor input that is used in establishing the minute ventilation delta signal fed over line 32 to the pulse generator 34 for adjusting the rate at which the pulse generator issues cardiac stimulating pulses to the heart.

The pacemaker 10 also includes an activity sensor in the form of an integrated silicon accelerometer 44 that is bonded to a ceramic circuit board contained within the housing of the CRM device. The accelerometer includes a mass suspended by four leaf spring elements from a frame. The springs each include a piezoresistive element forming the four legs of a Wheatstone bridge which becomes unbalanced from displacement of the mass due to acceleration forces in a direction perpendicular to the frame.

To conserve battery power, the Wheatstone bridge is energized in a pulse mode where a predetermined voltage is applied across it for only a short period of time, typically 15 microseconds, and at a repetition rate of about 146 Hz. The raw accelerometer output from device 44 is then amplified by amplifier 46 before being applied to a switched capacitor bandpass filter 48. The pass band of the filter 48 effectively excludes motion artifacts due to external noise while allowing passage of signal components whose frequencies are related to body motion due to exercise.

The output from the bandpass filter 48 is further signal processed by circuit 50 and then converted to a digital quantity by A/D converter 52 before being applied to the microprocessor 28.

The CRM device 10 further includes a telemetry circuit 54 of known construction which allows information stored in the microprocessor's RAM memory banks to be read out transcutaneously to an external monitor 56 for viewing by a medical professional. Moreover, the telemetry link 58 allows programmable operands of the pacemaker to be altered following implantation of the CRM device.

One way to measure the activity level of a person is to measure the amount of oxygen the person is consuming. However, as explained above it is difficult to obtain accurate measurement of the amount of oxygen a person consumes unless the person is evaluated with somewhat cumbersome metabolic rate measuring equipment. For people going about their normal activities in a non-laboratory setting, a different method of measuring the person's activity level is required.

Metabolic equivalents (METS) are a unit of energy expenditure that is proportional to work load or oxygen uptake ($VO_2$).1METS=3.5 ml/(kg min). At rest, a person uses approximately 1 MET. Walking at 3 miles per hour, a person uses approximately 3.3 METS. Although METS are used in this application for the units of energy expenditure, any units measuring the energy used by the body may be applicable.

A pacemaker having an accelerometer and/or a minute ventilation sensor such as that described above, when installed in a patient, can conveniently be used to gather data which can then be used to calculate the metabolic equivalent (MET) in the patient due to patient activity.

The data collected by the sensors may be averaged over a period of from about 8 seconds to about 16 seconds. Then the data is converted into MET data using a formula which accurately correlates the minute ventilation and/or the accelerometer data to MET data. Time averaged data over a period of 1 to 5 minutes, or over other time periods, may also be used to provide a running time change comparing MET data in a given time period to the pervious ones.

In the present invention the MET level is calculated by the microprocessor solving the following linear equation:

$$\mathrm{MET}=ax+b$$

Where a is a conversion factor, b is the resting MET level, which is usually defined as 1, and x is the averaged sensor signal from either the accelerometer sensor XL or from the minute ventilation sensor MV or from a blended or weighted value of these two sensors.

In studies conducted on a significant number of patients we have empirically determined that for an accelerometer based rate responsive pacer, the values of a and b should be about 0.0576 and 1 respectively. Hence, the formula for accelerometerbased METS is:

$$\mathrm{XL\ METS}=0.0576 * \mathrm{XL}+1$$

For a pacemaker having a minute ventilation sensor it was found to be preferred to use the value of a as a=0.0172 and the value for b of b=1 to calculate METS such that the formula for minute ventilation derived METS is:

MV METS=0.0172 * XL+1

The values used for a and b in the above formulas may change with the type of sensor used, the amplification of the sensor and the placement of the sensor in the body; however, the principle of operation will remain the same.

If the patient is on a treadmill, or otherwise has a known walking speed, V, then METS may be calculated as follows:

METS=a * XL *V+b

In one test sequence performed on a selected number of patients METS was found to be:

METS=0.0123* XL * V+1.

If the average sensor signal is sampled, for example, every 10 seconds, then there are 6 MET calculations per minute using the above formula. The data from each calculation can be stored for future reference. Of particular interest is data showing the daily maximum MET level, which comprises the maximum activity level sustained by the patient during the day. This information is useful to a physician for setting pacing parameters of the pacemaker for the patient.

Also of interest is a daily moving average of MET levels of the patient. This information may also be calculated and stored. The moving average is calculated as the average over the last n number of measurements. For example n may be 50 or 100 to provide a moving average over recent measurements.

In order to record exercise events, a 1 to 8 minute moving average and an amplitude threshold may be applied to the sensor signal, such that exercise events are counted and stored.

In accordance with the invention, the daily maximum data, daily moving average, 1–8 minute moving average, and exercise events totals and times may be compiled in any combination of useful statistical manner, for daily, weekly, monthly or yearly reports, or for whatever need there is for MET data to aid in the treatment of the patient.

The data can be programmed to be reported to the physician or other health care provider in any manner desired to give useful information about the patient's activity levels. The data may be displayed or printed in tabular form, as a graph, a histogram chart, or as a simple listing or data as collected chronologically. The long term history of the MET levels show the patient's activity patterns and the physician may use the data as a diagnostic tool to assess the efficacy of a treatment protocol.

The MET data may also be used in a rate adaptive CRM device to automatically adjust the rate of pacing in a pacemaker.

The accelerometer data and the minute ventilation data may be combined in a blending algorithm to provide METS values.

The microprocessor 10 may be programmed to average received signals from the sensors over a time period of on the order of 8 to 16 seconds, and then to calculate the METS from the signals received, according to the above conversion formula e programmed into the microprocessor.

The microprocessor is further programmed to store the data from each MET time period calculation along with the time it occurred and can compare the MET for each time period to determine the daily maximal MET level and then store the value and time thereof in a memory register for later readout. The microprocessor is also preferably programmed to calculate a daily 24 hour moving average MET value and to store that value and the date thereof in a predetermined memory register. For example, the microprocessor may be programmed to calculate a 1 to 8 minute moving average MET value and further, an amplitude threshold can be applied to the XL and/or MV sensor signals to detect when the threshold is exceeded, indicative of exercise events of a given intensity. The microprocessor can also be programmed to count and store the total number of exercise events and the time of occurrence and MET values of each such exercise event.

The microprocessor can also be programmed to provide daily, weekly, monthly or yearly reports and average the MET values over any time periods to suit the report data desired by the physician or health care provider to better monitor the patient. The microprocessor may determine minimum averages of exertion during rest periods, and average exertion for the entire day or portions of the day.

The maximum and averaged MET levels and exercise frequency data can be retrieved from the pacemaker by telemetry methods well known in the art.

The METS data can be presented to the physician or health care provider in various forms including, but not limited to, time charting, graphs and tables. The physician can then use the data to determine what the patient's activity patterns are and to what degree of exertion the patient has reached during an exercise regimen and how frequently the exercise events take place. From this, the physician can then readily determine the degree of wellness of the patient and change the treatment of the patient accordingly. Such treatment may include changes in pacemaker pacing setting, drug delivery, etc.

Alternatively the moving average MET values calculated by the pacemaker may be used to adaptively adjust the pacemaker automatically for the activity level currently being experienced by the patient.

Obviously, many modifications and variations of the present invention are possible in light of the above teachings. It is therefore to be understood that, within the scope of the appended claims, the invention may be practiced otherwise than as specifically described.

What is claimed is:

1. A method of measuring the metabolic equivalent (METS) relating to patient exercise comprising the steps of:
    (a) affixing a physiologic sensor to the patient that produces electrical signals proportional to the patient's activity level;
    (b) processing the electrical signals; and
    (c) calculating METS based upon the processed signals obtained in step (b).

2. The method of claim 1 wherein the physiologic sensor is a component of an implantable cardiac rhythm management device and the step of affixing comprises implanting the cardiac rhythm management device within the patient.

3. The method of claim 2 wherein the implantable cardiac rhythm management device comprises a rate adaptive pacemaker and further including the step of:
    (a) utilizing a signal proportional to the calculated METS as a rate controlling parameter of the rate adaptive pacemaker.

4. A method of measuring the metabolic equivalent (METS) relating to patient exercise comprising the steps of:
    (a) affixing one of a minute ventilation sensor and an accelerometer to the patient for producing electrical signals proportional to one of a patient's instantaneous respiratory rate and tidal volume and physical activity;

(b) averaging the amplitude of the electrical signals over a predetermined time interval; and (c) calculating METS as a linear regression of the average obtained in step (b).

5. The method of claim 4 wherein said one of a minute ventilation sensor and an accelerometer is a component of an implantable cardiac rhythm management device and the step of affixing comprises implanting the cardiac rhythm management device within the patient.

6. The method of claim 5 wherein the implantable cardiac rhythm management device comprises a rate adaptive pacemaker and further including the step of:

(a) utilizing a signal proportional to the calculated METS as a rate controlling parameter of the rate adaptive pacemaker.

7. A method for assessing a patient's well-being, comprising the steps of:

a) implanting in the patient a cardiac rhythm management device having a cardiac depolarization sensor, a physiologic sensor producing electrical signals proportional to patient activity, a pulse generator for applying stimulating pulses to the heart and a microprocessor-based controller coupled to received an output from the cardiac depolarization sensor and the electrical signals from the physiologic sensor for producing delta rate signals for the pulse generator;

b) storing the delta rate signals in a memory of the microprocessor-based controller;

c) computing an average of the stored delta rate signals over a first predetermined time interval; and d) computing in the microprocessor-based controller a metabolic equivalent (METS) as a linear regression of the computed average.

8. A method for assessing a patient's well-being comprising the steps of:

a) implanting in the patient a cardiac rhythm management device of the type including, means for sensing cardiac depolarizing signals, means for sensing transthoracic impedance and producing an electrical signal, pulse generator means for applying cardiac stimulating signals to the patient's heart, and a microprocessor-based controller coupled to receive the cardiac depolarizing signal and the electrical signals proportional to transthoracic impedance for producing control signals related to the patient's minute ventilation (MV), said control signals being connected to the pulse generator means for controlling the rate at which the cardiac stimulating signals are produced;

b) recording said control signals proportional to minute ventilation in a memory of the microprocessor-based controller;

c) computing an average of said control signals over a first predetermined time interval; and d) computing in the microprocessor-based controller a metabolic equivalent (METS) as a linear regression of said computed average.

9. The method of claim 8 wherein the linear regression of said computed average is represented by an equation METS=a $MV_{ave}$+b where a and b are empirically determined constants.

10. The method of claim 9 wherein a is in a range of from 0.014 to 0.035 and preferably about 0.0172 and where b is about 1.

11. The method of claim 8 and further including the step of:

e) recording in the memory at second predetermined intervals the maximum and the average METS values computed in step d) within an immediately preceding one of the second predetermined time intervals.

12. The method of claim 11 wherein the first predetermined intervals are measured in seconds and the second predetermined intervals in one of days and weeks.

13. The method of claim 11 and further including the step of:

f) transcutaneosly reading out the maximum and average of METS values recorded in the memory to an external monitor whereby long term history of METS levels representative of a patient's activity patterns and changes therein become available to a physician.

14. The method of claim 8 further including the step of comparing an amplitude of the control signal to a predetermined threshold value indicative of exercise activity and determining the length of time that the amplitude of the control signal exceeds said threshold value.

15. A method of assessing a patient's well-being, comprising the steps of:

a) implanting in the patient a cardiac rhythm management device of the type including, means for sensing cardiac depolarizing signals, an accelerometer for sensing body activity and producing electrical signals (XL) proportional thereto, a pulse generator for applying cardiac stimulating signals to the patient's heart, a microprocessor-based controller coupled to receive the cardiac depolarizing signals and the electrical signals proportional to body activity for producing rate control signals for the pulse generator;

b) recording the rate control signals proportional to body activity (XL) in a memory of the Microprocessor-based controller;

c) computing an average of said control signals over a first predetermined time interval; and d) computing the microprocessor-based controller a metabolic equivalent (METS) as a linear regression of said computed average.

16. The method of claim 15 wherein the linear regression of the computed average is represented by an equation METS=a $XL_{ave}$+b where a and b are empirically determined constants.

17. The method of claim 16 wherein a is in a range of from about 0.050 to 0.070 and preferably about 0.0576 and b is about 1.

18. The method of claim 15 and further including the steps of:

e) recording in the memory at second predetermined intervals the maximum and the average METS values computed in step d) within an immediately preceding one of the second predetermined intervals.

19. The method of claim 18 wherein the first predetermined intervals are measured in seconds and the second predetermined intervals are measured in one of days and weeks.

20. The method of claim 18 and further including the step of:

f) transcutaneously reading out the maximum and average METS values recorded in the memory of an external monitor whereby long-term history of METS levels representative of a patient's activity patterns and changes therein become available to a physician.

21. The method of claim 15 and further including the step of comparing an amplitude of the control signal to a predetermined threshold value indicative of exercise activity and determining the length of time that the amplitude of the control signal exceeds said threshold value.

22. An apparatus for assessing a patient's well-being comprising:
 a) a cardiac rhythm management device having a cardiac depolarization sensor and a physiologic sensor, said physiologic sensor producing electrical signals proportional to patient activity, a pulse generator configured to apply cardiac stimulating pulses to the heart and a microprocessor-based controller connected to receive cardiac depolarization signals picked up by the cardiac depolarization sensor and the electrical signals proportional to patient activity and providing a delta rate signal to the pulse generator;
 b) a memory in the microprocessor-based controller for at least temporarily storing the delta rate signals,
 c) a microprocessor in the microprocessor-based controller coupled to the memory for reading out the stored delta rate signals and computing an average thereof over a first predetermined time interval; and
 d) said microprocessor computing a METS value as a linear regression of the computed average.

23. The apparatus of claim 22 wherein the physiologic sensor is a transthoracic impedance sensor.

24. The apparatus of claim 23 wherein the delta rate signal is proportional to the patient's minute ventilation (MV).

25. The apparatus of claim 24 wherein the linear regression is calculated as:

$$METS = a\ MV_{ave} + b$$

where $MV_{ave}$ is an average delta rate signal over said predetermined time interval, and a and b are empirically derived constants.

26. The apparatus of claim 25 wherein a is in a numerical value in a range of from 0.014 to 0.035 and preferably about 0.0172 and b is about 1.

27. The apparatus of claim 22 wherein the physiologic sensor is an accelerometer.

28. The apparatus of claim 27 wherein the delta rate signal is proportional to the patient's motion.

29. The apparatus of claim 28 wherein the linear regression is calculated as:

$$METS = a\ XL_{ave+b}$$

where $XL_{ave}$ is an average delta rate signal over said predetermined time interval and a and b are empirically derived constants.

30. The apparatus of claim 29 wherein a is a numerical value in a range of from about 0.050 to 0.070 and preferably about 0.0576 and b is about 1.

31. The apparatus of claim 22 and further including:
 e) means for storing in said memory at second predetermined time intervals the maximum and the average METS values computed in the microprocessor within an immediately preceding one of the second predetermined time intervals.

32. The apparatus of claim 31 and further including:
 f) a telemetry link in the cardiac rhythm management device adapted to transcutaneously read out from the memory said maximum and average METS values to an external monitor.

33. An apparatus for assessing a patient's well-being comprising:
 a) an implantable electronics module having a physiologic sensor producing electrical signals proportional to a patient's physical activity, a microprocessor coupled to receive the electrical signals from the sensor and programmed to solve for a METS value a linear regression formula having as an independent variable an average over a predetermined time interval of the electrical signal, and a telemetry channel.
 b) an external monitor adapted to communicate with the implantable module over the telemetry channel.

34. The apparatus of claim 33 wherein the physiologic sensor includes an accelerometer.

35. The apparatus of claim 34 wherein the physiologic sensor produces said electrical signal, said electrical being proportional to the patient's minute ventilation.

36. An apparatus for measuring the metabolic equivalent (METS) relating to patient exercise comprising:
 (a) an accelerometer affixed to the patient for producing electrical signals proportional to the patient's instantaneous activity levels;
 (b) a circuit for averaging an amplitude of the electrical signals over a predetermined time interval; and
 (c) means for calculating a METS value as a linear regression of the averaged amplitude of the electrical signals.

37. The apparatus of claim 36 wherein the accelerometer is a component of an implantable cardiac rhythm management device.

38. The apparatus of claim 37 wherein the cardiac rhythm management device comprises a rate adaptive pacemaker and the METS value comprises a rate controlling parameter for the rate adaptive pacemaker.

39. An apparatus for measuring the metabolic equivalent (METS) relating to a patient's exercise comprising:
 (a) a minute ventilation sensor affixed to the patient for producing electrical signals having an amplitude proportional thereto;
 (b) a circuit for averaging the amplitude of the electrical signals over a predetermined time interval; and
 (c) means for calculating a METS value as a linear regression of the averaged amplitude of the electrical signals.

40. The apparatus of claim 39 wherein the minute ventilation sensor is a component of an implantable cardiac rhythm management device.

41. The apparatus of claim 40 wherein the cardiac rhythm management device comprises a rate adaptive cardiac pacemaker and the METS value comprises a rate controlling parameter for the rate adaptive pacemaker.

* * * * *

UNITED STATES PATENT AND TRADEMARK OFFICE
CERTIFICATE OF CORRECTION

PATENT NO. : 6,273,856 B1
DATED : August 14, 2001
INVENTOR(S) : Weimin Sun et al.

It is certified that error appears in the above-identified patent and that said Letters Patent is hereby corrected as shown below:

Column 8, claim 15,
Line 33, the word "Microprocessor-based" should read -- "microprocessor-based" --

Colum 9, claim 29,
Line 30, in the equation, "+b" should not be superscript.

Column 10, claim 35,
Line 21, the word "signal" is missing after the words "said electrical"

Signed and Sealed this

Ninth Day of April, 2002

Attest:

Attesting Officer

JAMES E. ROGAN
Director of the United States Patent and Trademark Office